United States Patent [19]

Cross et al.

[11] Patent Number: 5,215,706
[45] Date of Patent: Jun. 1, 1993

[54] METHOD AND APPARATUS FOR ULTRASONIC TESTING OF NUCLEAR FUEL RODS EMPLOYING AN ALIGNMENT GUIDE

[75] Inventors: Howard D. Cross, Kennewick; Leo E. Hansen, Bellevue; Richard G. McClelland, Richland, all of Wash.

[73] Assignee: Siemens Power Corporation, Bellevue, Wash.

[21] Appl. No.: 710,418

[22] Filed: Jun. 5, 1991

[51] Int. Cl.$^5$ ............................................. G21C 17/07
[52] U.S. Cl. .................................. 376/252; 376/245; 73/620; 73/627
[58] Field of Search ........................... 376/245, 252; 976/DIG. 207, DIG. 231, DIG. 232, DIG. 235, DIG. 236; 73/620, 627, 628, 629

[56] References Cited

U.S. PATENT DOCUMENTS

| | | | |
|---|---|---|---|
| 3,901,090 | 8/1975 | Akey et al. | 73/67.2 |
| 4,036,686 | 7/1977 | Weilbacker et al. | 176/19 R |
| 4,174,255 | 11/1979 | Lawrie | 176/19 LD |
| 4,193,843 | 3/1980 | Womack et al. | 176/19 LD |
| 4,313,791 | 2/1982 | Lawrie et al. | 376/252 |
| 4,517,152 | 5/1985 | Pieper et al. | 376/252 |
| 4,605,531 | 8/1986 | Leseur et al. | 376/252 |
| 4,637,912 | 1/1987 | Scharpenberg et al. | 376/245 |
| 4,645,634 | 2/1987 | Roseveare | 376/245 |
| 4,650,637 | 3/1987 | Chubb | 376/253 |
| 4,655,993 | 4/1987 | Scharpenberg | 376/252 |
| 4,657,728 | 4/1987 | Coppa et al. | 376/245 |
| 4,683,104 | 7/1987 | Scharpenberg | 376/251 |
| 4,696,784 | 9/1987 | Tolino et al. | 376/245 |
| 4,728,483 | 3/1988 | Ahmed et al. | 376/258 |
| 4,741,878 | 5/1988 | Gebelin et al. | 376/248 |
| 4,816,207 | 3/1989 | Scharpenberg | 376/252 |
| 4,847,036 | 7/1989 | Scharpenberg et al. | 376/245 |
| 4,847,037 | 7/1989 | Scharpenberg et al. | 376/245 |
| 4,879,088 | 11/1989 | van Swam et al. | 376/252 |
| 4,892,701 | 1/1990 | Mauvieux et al. | 376/258 |
| 4,895,765 | 1/1990 | Sue et al. | 428/627 |

FOREIGN PATENT DOCUMENTS

| | | | |
|---|---|---|---|
| 63681 | 11/1982 | European Pat. Off. | 376/252 |
| 0095553 | 1/1983 | European Pat. Off. | |
| 0082102 | 6/1983 | European Pat. Off. | |
| 0178860 | 4/1986 | European Pat. Off. | |
| 0261563 | 10/1988 | European Pat. Off. | |
| 0329554 | 8/1989 | European Pat. Off. | |

Primary Examiner—Donald P. Walsh
Assistant Examiner—Chrisman D. Carroll
Attorney, Agent, or Firm—Ira Lee Zebrak

[57] ABSTRACT

A method and apparatus for eliminating erroneous test readings during ultrasonic testing of nuclear fuel rods is disclosed. The method and apparatus employ the use of an alignment guide to effect temporary alignment of the fuel rods during testing in order to overcome mechanical deviations of the rods. The alignment guide includes elongated, parallel guide bars for insertion into an array prior to ultrasonic testing. The bars are mounted on a base which, in turn, is movably mounted on a support element. A fixed guide maintains the relative position of the guide bars with respect to one another. A hydraulic element causes the guide bars to be inserted and removed from the fuel array. In a preferred arrangement, the alignment guide may be removably mounted on a frame containing the ultrasonic testing equipment.

19 Claims, 5 Drawing Sheets

35

35

METHOD AND APPARATUS FOR ULTRASONIC TESTING OF NUCLEAR FUEL RODS EMPLOYING AN ALIGNMENT GUIDE

BACKGROUND OF THE PRESENT INVENTION

1. Field of the Present Invention

The present invention relates to the field of testing of nuclear fuel rods and, in particular, to improvements in the testing of nuclear fuel rods by ultrasonic techniques.

2. Background Prior Art

The use of ultrasonic energy for detecting defects in nuclear fuel rods is known. U.S. Pat. Nos. 4,174,255 and 4,517,152 are two patents disclosing such use of ultrasonic energy for testing of nuclear fuel rods.

In U.S. Pat. No. 4,879,088, assigned to the same assignee as that of the present invention, nuclear fuel rods are checked for defects by ultrasonic pulses emitted from a transducer. Such fuel rods, which form the core of the reactor, are elongated elements. The rods typically have diameters of about ⅜ to ½ inch, are about 10 to 12 feet long and are grouped in bundles which are generally square. Each rod is formed of cladding of zirconium alloy or stainless steel, which is filled with uranium dioxide, typically in the form of pellets. The remainder of the space within the cladding is commonly filled with helium. During the operation of the reactor, holes may develop in the cladding due to stress, corrosion, wear or defective welding to the end plugs which close the ends of the cladding tubes. If this occurs, the helium and fusion gases will escape into the cooling water of the reactor and the water will enter the cladding tubes.

According to the approach of U.S. Pat. No. 4,879,088, a transducer is caused to traverse a fuel assembly consisting of a group of fuel rods. During the traverse, a series of ultrasonic pulses is emitted from the transducer in the form of a beam. When the beam strikes a fuel rod, it is reflected from the outer surface. If the beam is exactly normal to the surface, it will be reflected back into the transducer to a maximum degree which will give rise to an electrical signal ("pulse-echo" technique). Part of the ultrasonic energy penetrates the cladding but the normal rod does not pass ultrasonic energy (the internal gas and uranium dioxide are non-conductive) resulting in "wall ringing" between inner and outer walls of the rod. The wall ringing is recorded. If the rod is filled with water, there will be a transfer of the ultrasonic energy from the tubing wall into the water where it is effectively dispersed. This greatly attenuates the wall ringing. This will occur whether uranium dioxide is present or not. The attenuation of the wall ringing identifies a defective fuel rod.

In practice, test results employing the ultrasonic approach of fuel rod testing have indicated erroneous readings under certain circumstances. Such erroneous readings lead to conclusions that specific fuel rods indicate failure, when in fact they were properly functioning.

Further study of the fuel rod assembly suggests that differences in fuel rod and guide tube diameters (in the case of PWR fuel assemblies) and fuel rod bow, will cause alignment problems of the rods leading to the erroneous ultrasound readings. While U.S. Pat. No. 4,847,037 to Scharpenburg does recognize that bowing of fuel rods occurs, there is no suggestion for providing pre-alignment to all fuel rods of an assembly to correct for such bowing.

SUMMARY OF THE PRESENT INVENTION

It is an object of the present invention to avoid erroneous readings in ultrasonic testing of nuclear fuel rods.

It is a further object of the present invention to provide apparatus to pre-align fuel rod assemblies for avoiding erroneous readings in ultrasonic testing of nuclear fuel rods.

It is another object of the present invention to overcome misalignment in fuel rod assemblies caused by differences in fuel rod and guide tube diameters and fuel rod bow which cause erroneous readings in ultrasonic testing of nuclear fuel rods.

In accordance with the invention, a method is provided for the ultrasonic testing of a nuclear fuel rod array with attendant suppression of erroneous readings comprises the steps of aligning the individual rods of a fuel rod array with respect to one another, providing a source of ultrasonic energy and applying said source to a fuel rod of an aligned fuel rod array and determining whether a fuel rod of an aligned assembly is operationally acceptable by developing a signal representing the conduction of ultrasonic energy within the rod. In a particular form of the method, the providing and determining steps of an aligned fuel rod array are repeated for each rod of the array.

Further in accordance with the invention, an arrangement for the ultrasonic testing of a nuclear fuel rod array with attendant suppression of erroneous readings comprises means for aligning the individual rods of a fuel rod array with respect to one another prior to ultrasonic testing of the fuel rod array, means for supplying ultrasonic energy to a fuel rod of a fuel rod assembly for testing whether the rod is operationally acceptable, means for developing a signal representative of whether a fuel rod is operationally acceptable upon application of ultrasonic energy to the fuel rod and means for causing the ultrasonic energy supplying means to traverse the fuel rod array to permit testing of each rod of the array. Accordingly, alignment of the fuel rod array prior to ultrasonic testing suppresses tendencies to produce erroneous test readings caused by mechanical deviations of individual fuel rods.

For a better understanding of the present invention, reference is made to the following description and accompanying drawings while the scope of the invention will be pointed out in the appended claims.

DESCRIPTION OF THE PREFERRED EMBODIMENTS

Figure 1:
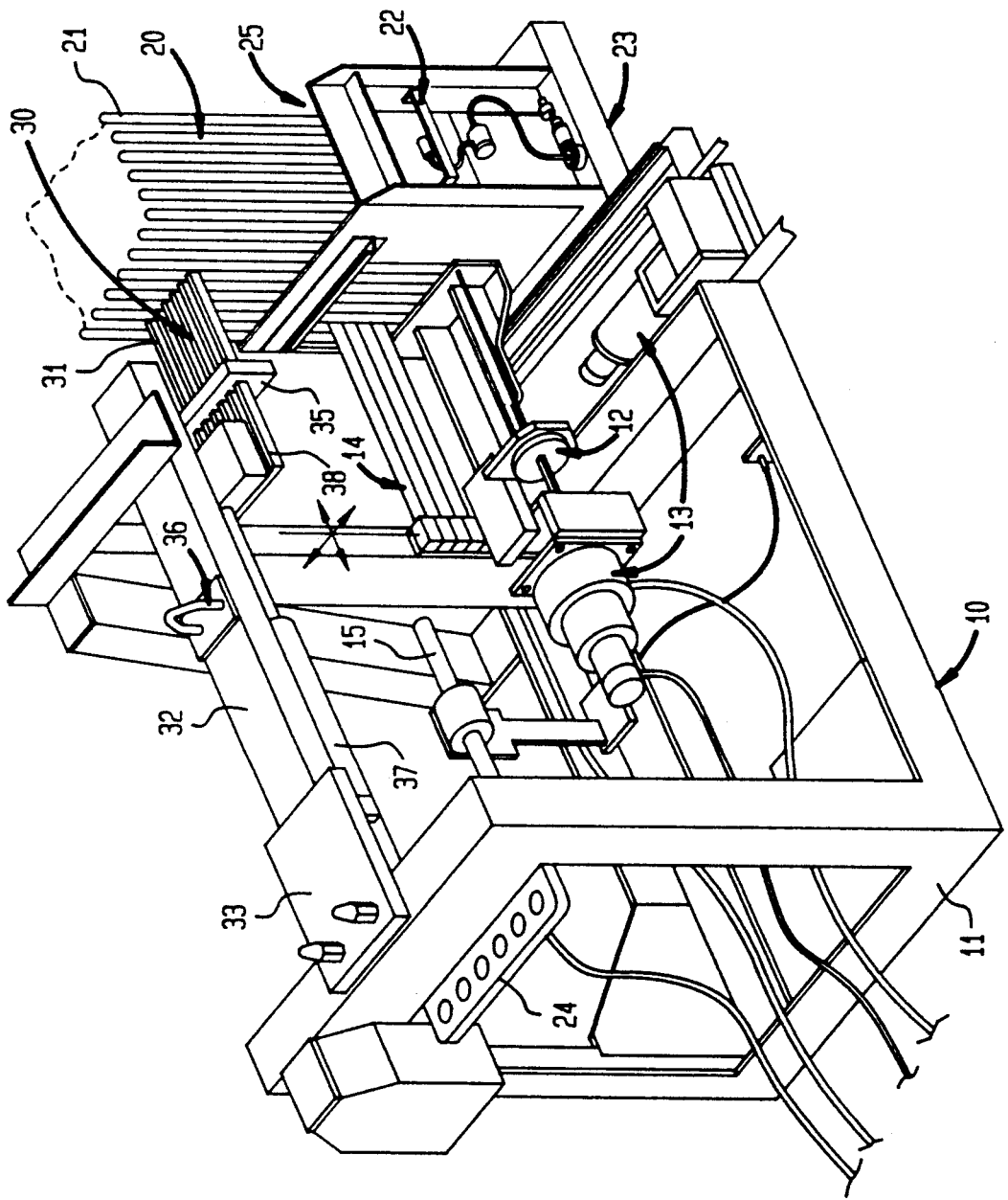
FIG. 1 is a perspective view of ultrasonic testing equipment for testing the operational acceptability of fuel rods in accordance with the invention.
Figure 2:
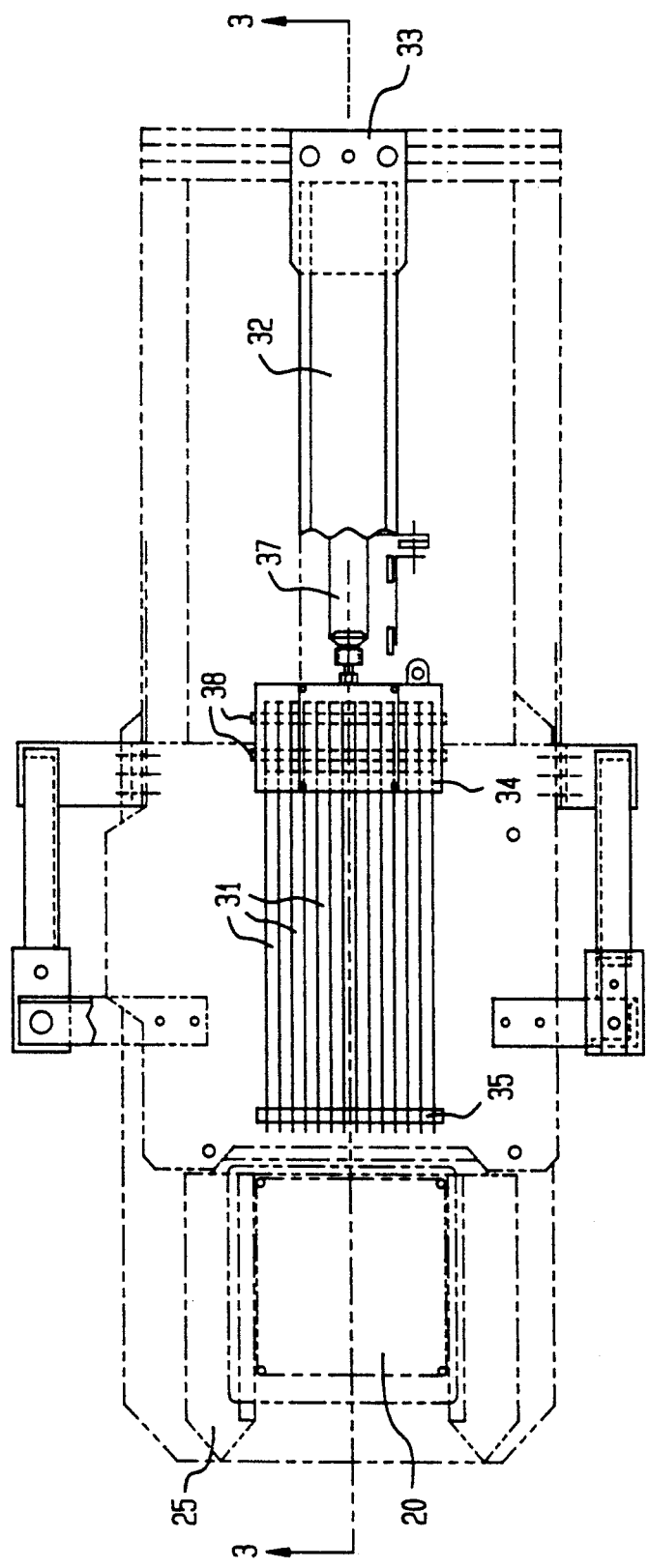
FIG. 2 is a plan view of the ultrasonic testing equipment of FIG. 1.
Figure 3:
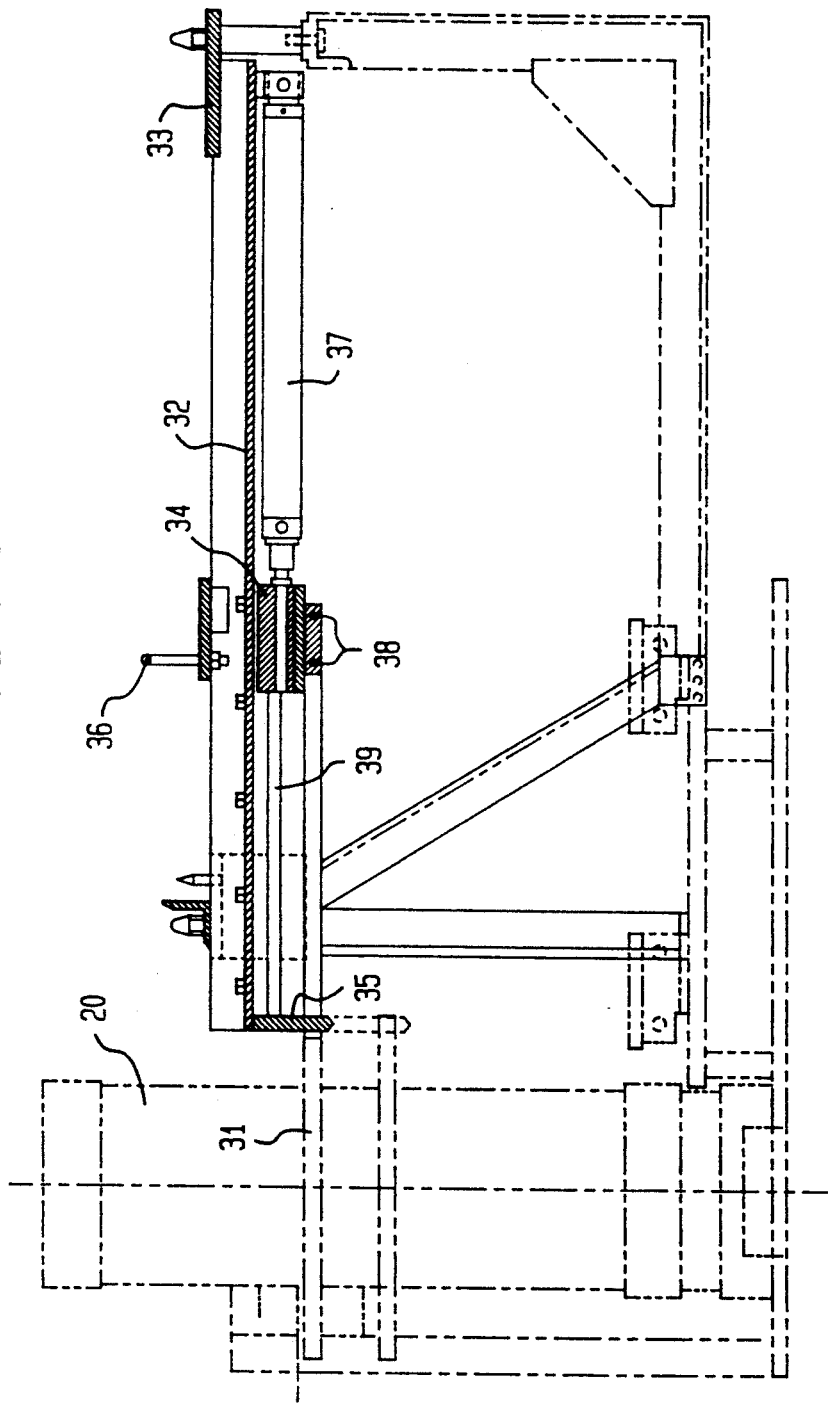
FIG. 3 is a side, cross-sectional view along A—A of FIG. 2.

Referring initially to FIGS. 1, 2 and 3, shown there is an ultrasonic testing device 10 for determining the functional operability of individual fuel rods 21 of a fuel rod assembly 20.

The fuel rod assembly 20 is supported by an upper plate (not shown) which is attached to an overhead crane. The assembly 20 is arranged within an assembly positioning channel 25 which is a U-shaped construction having a retractable side plates 22 and a base plate 23. The assembly is preferably arranged as a rectangular grouping of fuel rods.

As discussed previously, the rods 21 contain uranium dioxide and helium gas disposed within a metallic cladding (typically zirconium alloy or stainless steel). The ultrasonic testing for water entry within the rods is performed by juxtaposition of ultrasonic probes 14 to each individual fuel rod within the assembly in succession. The probes 14 test only one lower portion ("test spot") of each rod. It is not necessary to test the entire rod.

The ultrasonic probes 14 (here 4 are shown operating together) are movable in a horizontal plane by X-Y table 12. The X-Y table 12 positions the ultrasonic probes 14 by virtue of drive motors 13. Thus, the probes may be inserted and retracted from the fuel rod assembly to enable testing of each fuel rod in the assembly. Control over movement of the probes 14 is effected from a control console (not shown) connected to the X-Y table via cable connection 24, by depressing appropriate control switches.

The present invention utilizes a plurality of parallel guide bars 31 for insertion between individual fuel rods prior to the start of any ultrasonic testing of the fuel rods. The guide bars 31 are part of a guide assembly 30 which includes holding base 34, bars 31, channel element 32, flange 33, front guide 35, lifting bale 36, hydraulic cylinder 37 and pins 38.

The guide bars 31 are preferably constructed of heat treated Inconel which is provided with a hard coat of titanium nitride to minimize surface abrasion. The guide bars 31 are held in relative position by two pins 38 through holding base 34. A front guide 35, which is fixed in position relative to the movable guide bars 31, serves to maintain the bars in relative position as they are caused to move in and out of the fuel assembly. The alignment guide 30 is supported by a channel element 32 which is affixed via flange 33 to frame 11 of the X-Y table. Twin rail linear bearings 39 (see FIG. 3) are affixed to the underside of the channel element 32 for supporting the guide bar holding base. Fixed front guide 35 is also attached to the underside of the channel element 32. Power for moving the guide bars in and out is provided by a hydraulic cylinder 37. The entire alignment guide 30 is removable from the frame 11 with the assistance of lifting bale 36.

In operation, it has been found useful to provide a TV camera 15 forming part of TV monitoring system to assure proper alignment of guide rods 31 between the fuel assembly fuel rods.

It should be noted that the guide rods 31 are preferably inserted into the fuel assembly immediately above the test spot where the ultrasonic probes enter the fuel assembly. This temporarily skews the fuel rod arrangement in the fuel assembly into alignment prior to insertion of the ultrasonic probes. The guide bars are preferably inserted completely through a fuel assembly prior to ultrasonically testing each individual row of fuel rods.

Figure 4:
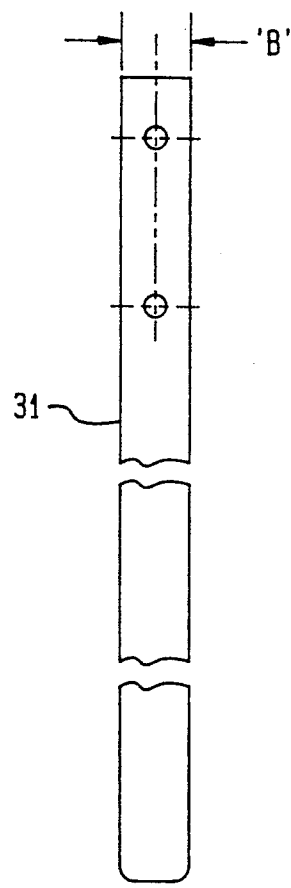
FIG. 4 is a side-view and FIG. 5 is a top-view of a guide bar of the present invention.
Figure 5:
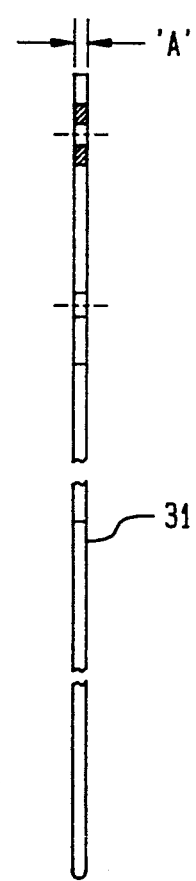

In a preferred arrangement as shown in FIGS. 4 and 5, the guide bars 31 are in the form of elongated blades having a small width dimension "A", corresponding to inter-rod spacings and a substantial larger height dimension "B". In one embodiment, the height dimension was approximately 0.75 inches. The width dimension will vary from one fuel rod to another but will typically be in the range of 0.061 inches to 0.124 inches.

Figure 6:
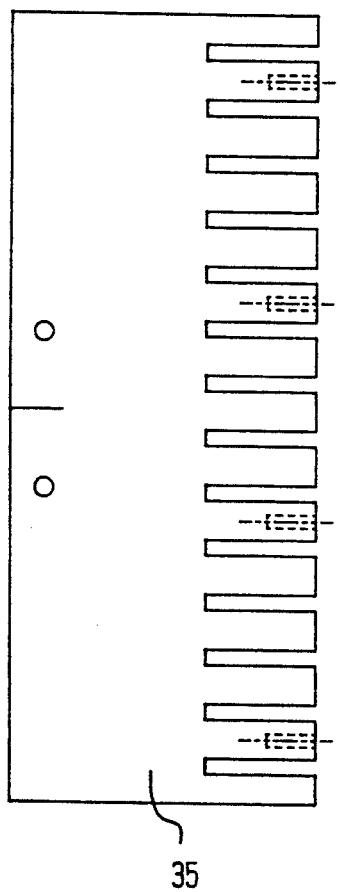
FIG. 6 is a side-view and FIG. 7 is a plan view of a fixed front guide in accordance with the present invention.
Figure 7:
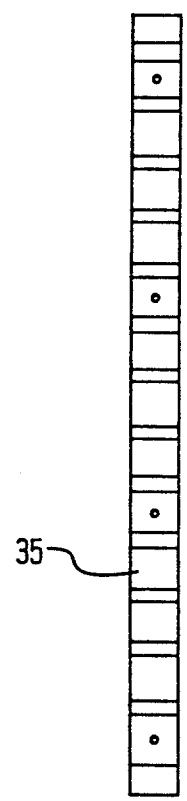

A preferred form of the fixed front guide 35 is illustrated in FIG. 6 and 7.

In one set of tests, six fuel assemblies were retested employing a guide assembly according to the invention, after each showed failure of one fuel rod by ultrasonic testing without the assembly. Following retest with the guide assembly, four fuel assemblies tested "good" (functionally operable) while only two were confirmed to have a failed fuel rod.

While the foregoing description and drawings represent the preferred embodiments of the present invention, it will be obvious to those skilled in the art that various changes and modifications may be made therein without departing from the true spirit and scope of the present invention.

What is claimed is:

1. A method for the ultrasonic testing of a nuclear fuel rod array forming part of a fuel assembly with attendant suppression of erroneous readings comprising the steps of:

aligning the individual rods of a fuel rod array with respect to one another;

providing a source of ultrasonic energy and applying said source to a fuel rod of said aligned fuel rod array; and following application of ultrasonic energy to said fuel rod, determining whether a fuel rod of said aligned array is operationally acceptable by developing a signal representing the conduction of ultrasonic energy within the rod.

2. The method of claim 1 including repeating said providing and determining steps of an aligned fuel rod array for each rod of the array.

3. The method of claim 1 wherein said aligning step includes providing a plurality of guide bars and inserting said guide bars completely through the array.

4. A method for the ultrasonic testing of a nuclear fuel rod array with attendant suppression of erroneous readings comprising the steps of:

aligning the individual rods of a fuel rod array with respect to one another;

providing a source of ultrasonic energy and applying said source to a fuel rod of the aligned fuel rod array;

determining whether a fuel rod of an aligned array is operationally acceptable by developing a signal representing the conduction of ultrasonic energy within the rod, and wherein said aligning step includes providing a plurality of guide bars and inserting said guide bars completely through the array and wherein inserting of said guide bars is performed immediately above a portion of said array where ultrasonic application is applied to a fuel rod.

5. An arrangement for the ultrasonic testing of a nuclear fuel rod array forming part of a fuel assembly with attendant suppression of erroneous readings comprising:

means for aligning the individual rods of a fuel rod array with respect to one another prior to ultrasonic testing of the fuel rod array;

means for supplying ultrasonic energy to a fuel rod of said fuel rod array following alignment for testing whether the rod is operationally acceptable;

means for developing a signal representative of whether a fuel rod is operationally acceptable upon application of ultrasonic energy to the fuel rod; and means for causing said ultrasonic supply means to traverse the fuel rod array to permit testing of each rod of said array;

whereby alignment of the fuel rod array prior to ultrasonic testing suppresses the tendencies to produce erroneous test readings caused by mechanical deviations of individual fuel rods.

6. An arrangement according to claim 5, wherein said alignment means includes a plurality of elongated guide bars for insertion in spaces between fuel rods of the fuel array for aligning the fuel rods.

7. An arrangement according to claim 6 wherein said guide bars are affixed to holding means and wherein said hydraulic means are provided for moving said holding means into and out of said fuel array.

8. An arrangement according to claim 6 wherein said array is arranged in rectangular form with said rods disposed in rows and columns and wherein said alignment means provides the capability of insertion of said guide bars completely through said fuel array prior to ultrasonic testing.

9. An arrangement according to claim 7 wherein fixed guide means are provided to maintain the relative position of the guide bars as they are inserted and removed from the fuel array.

10. An arrangement for the ultrasonic testing of a nuclear fuel rod array with attendant suppression of erroneous readings comprising:

means for aligning the individual rods of a fuel rod array with respect to one another prior to ultrasonic testing of the fuel rod array, said alignment means including a plurality of elongated guide bars for insertion in spaces between fuel rods of the fuel array for aligning the fuel rods, said guide bars being arranged immediately above a portion of said fuel array where ultrasonic testing of a fuel rod takes place;

means for supplying ultrasonic energy to a fuel rod of a fuel rod assembly for testing whether the rod is operationally acceptable;

means for developing a signal representative of whether a fuel rod is operationally acceptable upon application of ultrasonic energy to the fuel rod;

means for causing said ultrasonic supply means to traverse the fuel rod array to permit testing of each rod of said array;

whereby alignment of the fuel rod array prior to ultrasonic testing suppresses tendencies to produce erroneous test readings caused by mechanical deviations of individual fuel rods.

11. An arrangement for the ultrasonic testing of a nuclear fuel rod array with attendant suppression of erroneous readings comprising:

means for aligning the individual rods of a fuel rod array with respect to one another prior to ultrasonic testing of the fuel rod array;

means for supplying ultrasonic energy to a fuel rod of the fuel rod array for testing whether the rod is operationally acceptable;

means for developing a signal representative of whether a fuel rod is operationally acceptable upon application of ultrasonic energy to the fuel rod;

means for causing said ultrasonic supply means to traverse the fuel rod array to permit testing of each rod of said array; and wherein said alignment means includes a plurality of elongated guide bars for insertion in spaces between fuel rods of the fuel array for aligning the fuel rods, and including means for providing closed circuit television monitoring of the insertion of the guide rods into and removal from the fuel array.

12. An arrangement for the ultrasonic testing of a nuclear fuel rod array with attendant suppression of erroneous readings comprising:

a frame;

an X-Y table supported by said frame;

an ultrasonic assembly movable by said X-Y table, said assembly having a plurality of ultrasonic probes for testing fuel rods of a fuel rod array to determine functional operability;

an alignment guide mounted on said frame above said ultrasonic assembly, said alignment guide including:

a support;

a base mounted on said support for movement toward and away from a fuel rod array;

a plurality of elongated guide bars mounted on said base for insertion between fuel rods of a fuel rod array and removal therefrom; and means mounted on said support for moving said base with said guide bars toward and away from a fuel rod array.

13. The arrangement of claim 12 also including a fixed guide mounted on said support for maintaining the relative position of the guide rods.

14. The arrangement of claim 12 wherein said guide bars are substantially parallel to each other and each bar is equidistant from immediately adjacent bars.

15. The arrangement of claim 12 wherein said alignment guide is removably mounted from said frame.

16. An alignment guide for use with equipment for ultrasonic testing of a nuclear fuel rod array for suppressing erroneous test readings comprising:

a support;

a base mounted on said support for movement toward and away from a fuel rod array;

a plurality of elongated guide bars mounted on said base for insertion between fuel rods of a fuel rod for aligning the fuel rods of the array prior to ultrasonic testing; and means mounted on said support for moving said base with said guide bars toward and away from a fuel rod array.

17. The alignment guide of claim 16 also including a fixed guide mounted on said support for maintaining the relative position of the guide bars.

18. The alignment guide of claim 16 wherein said guide bars are substantially parallel to each other and each bar is equidistant from immediately adjacent bars.

19. The alignment guide of claim 16 wherein said elongated guide bars are in the form of blades.

* * * * *